United States Patent [19]

Wrasidlo et al.

[11] Patent Number: 4,956,289
[45] Date of Patent: Sep. 11, 1990

[54] THIN FILM MEMBRANE ENZYME REACTOR AND METHOD OF USING SAME

[75] Inventors: Wolfgang J. Wrasidlo, LaJolla; Frieder K. Hofmann, Oceanside, both of Calif.

[73] Assignee: Brunswick Corporation, Skokie, Ill.

[21] Appl. No.: 26,380

[22] Filed: Mar. 16, 1987

[51] Int. Cl.⁵ .................... C12N 11/02; C12N 11/08; C12N 11/14

[52] U.S. Cl. .................... 435/180; 210/632; 435/176; 435/177; 435/182; 435/817

[58] Field of Search .............. 435/176-182, 435/240, 241, 243, 817; 210/632, 651, 456, 489, 488, 490

[56] References Cited

U.S. PATENT DOCUMENTS

| | | | |
|---|---|---|---|
| 3,979,274 | 9/1976 | Newman | 210/490 |
| 4,307,195 | 12/1981 | Karasawa et al. | 435/182 |
| 4,404,066 | 9/1983 | Johnson | 435/817 |
| 4,545,382 | 10/1985 | Higgens et al. | 435/180 |
| 4,795,704 | 1/1989 | Matson | 435/179 |

FOREIGN PATENT DOCUMENTS

| | | |
|---|---|---|
| 0242997 | 8/1985 | Czechoslovakia . |
| 0036315 | 9/1981 | European Pat. Off. . |
| 0112812 | 7/1985 | European Pat. Off. . |

Primary Examiner—Robert J. Hill, Jr.
Attorney, Agent, or Firm—Waldron & Associates

[57] ABSTRACT

An enzyme reactor system is provided based on the entrapment of an enzyme in a hydrogel layer coated on a support, and confined by an ultraporous thin film membrane diffusion barrier. The diffusion barrier confines the enzyme, but lets substrate and reaction products diffuse feeely into and out of the hydrogel layer. In an alternate embodiment, the support is formed of an ultraporous thin film membrane diffusion barrier on a microporous or macroporous support, through which the reaction products can diffuse freely, but through which neither enzyme nor substrate can pass. In this embodiment, the product is recovered in high purity, free of substrate and enzyme.

28 Claims, 2 Drawing Sheets

THIN FILM MEMBRANE ENZYME REACTOR AND METHOD OF USING SAME

BACKGROUND OF THE INVENTION

This application relates to thin film membrane enzyme reactors.

More particularly, this application relates to thin film membranes, preferably ultraporous, formed of cross linked polymer systems, and to methods and techniques for the utilization of such membranes for confining active enzymes as enzyme reactor structures, and the manufacture and use thereof.

In addition, this application relates to composite ultraporous thin film membranes, having an ultraporous thin film membrane diffusion barrier confining an active enzyme formulation supported on a support, and to methods and techniques for the manufacture thereof.

Most common, industrial, enzymatic reactions are carried out in bulk reaction systems, ordinarily in batch reactions. The enzyme component which catalyzes the desired reaction is usually discarded as waste at the conclusion of the reaction. This occurs even though the enzyme functions as a catalyst and theoretically it is therefore possible to recover and recycle the enzyme at the conclusion of the reaction. However, in actual industrial scale reactions the theoretically possible recovery and recycling steps are rarely, if ever, carried out. Apart from the expense of recovery, it has often been found that the activity of recovered and recycled enzymes is degraded by the recovery procedures and in many cases undesirable or intolerable contaminants are introduced. Thus for many industrial enzymatic procedures, batch operations in bulk remain the norm.

For many enzyme catalyzed processes, the desirability and need for continuous, as opposed to batch, processing and other features has led to extensive investigations of techniques and means for the immobilization of enzymes on supports of one kind or another. The most commonly employed procedure at present is glutaraldehyde immobilization by the formation of covalent bonds to the enzyme, which form the basis for cross-linking the product to a physical support. The support is most often a granular solid, although there have been numerous investigations and use of other forms of supports, including membrane supports, particularly to physically entrap enzymes within the pores of membrane structures, most often with the additional use of chemical immobilization. It has been observed, however, that in many systems enzyme activity is impaired or even completely lost as a consequence of interference of the covalent cross-linking with the reactive site of the enzyme. There have been observations which reveal that the temperature and pH optima are also altered by such procedures. In some circumstances, advantage may be taken of the changes in properties, but on the whole, it is desirable to provide a technique which retains the original properties of the enzyme to the greatest possible degree.

In other contexts, there have been investigations of systems for physical entrapment or encapsulation of enzymes. The objectives of these procedures have generally been to avoid the unfavorable consequences of covalent bonding immobilization procedures, while retaining the advantages thereof. These systems and approaches have met with limited success and acceptance for a variety of reasons. Among these are characteristics which result in the loss of direct and intimate contact between the enzyme and the substrate, because of the limited diffusion capacities of such materials and structures, with the attendant losses in production rate and efficiency, and the rather substantial cost penalties involved.

One approach to physical entrapment of enzymes has been to confine the material on or in a membrane structure, where the enzyme remains lodged while the substrate is flowed through the membrane. The resulting stream is processed to recover the product, and the substrate is recycled. By these techniques the art has attempted to provide direct and intimate contact between the enzyme and the substrate, and by using commercially available membranes, the cost of this type of immobilization are kept to a reasonable level. These techniques have not met with acceptance, however, since the efficiencies of the system may be impaired in other ways. Notably, there is a trade-off between the permeability of the membrane, i.e., the resistance to flow of the substrate process stream, and the effectiveness of the containment of the enzyme. When the controlling or limiting pore size of the membrane is optimal for confining the enzyme, the hydraulic resistance to flow of the substrate containing stream is often unacceptably high. When the pore size is enlarged to a level more consistent with the flow rates required for reasonable through-put, there is an increasing risk of enzyme loss into the product stream. In some circumstances, the result is an inconvenient burden on the product purification, but in other circumstances, such results are intolerable.

OBJECTS OF THE INVENTION

It is an object of the present invention to provide ultraporous thin film membrane enzyme reactors.

Another object of the present invention is to provide ultraporous thin film membrane enzyme reactors made from a diversity of polymers.

Still another object is to provide ultraporous thin film membrane enzyme reactors which are durable and effective for diffusion driven enzyme reactions.

Yet another object of the present invention is to provide a physically immobilized enzyme with high reaction catalyzing activity for a substrate in a process flow stream, wherein the enzyme is entrapped within a thin film membrane reactor having a large enzyme concentration, high diffusive permeability to specific substrate and product materials, and stable activity for a long operating period.

Another object of the present invention is to provide a reactor construction for enzyme catalyzed and/or mediated reactions having an enzyme gel layer confined on the support by a thin film porous membrane.

It is another object of the present invention to provide techniques for the production of ultraporous thin film membrane enzyme reactors.

It is yet another object of the present invention to provide techniques for the effective, reproducible production of high quality, uniform and effective thin film membrane enzyme reactors with controlled diffusion properties.

SUMMARY OF THE INVENTION

Enzymes are applied to a support surface in the form of a hydrogel, which is in turn covered with a thin film polymer membrane having a high porosity for the reaction substrate and water, and for the reaction product, but which is impermeable to the enzyme. The thin film will most often have a pore size in the ultraporous range, i.e. from about 0.0005 to 0.1 microns, consistent with the dimensions of substrate molecules to be reacted and the product molecules produced. Such membranes have high permeability to water, but will not pass large molecules, such as the enzyme.

Ultraporous thin film membrane diffusion barriers are provided for use in the present invention by controlled cross linking of polymer films of substantially monomolecular thickness by techniques which afford control over the cross link density in the thin film, achieved by regulating the cross link determinants of the polymer system. The resulting thin films, with the requisite cross link density are ultraporous, and range in thickness from monomolecular, i.e., on the order of 0.0012 or 0.0015 microns, up to about 0.15 microns, more often up to about 0.2 microns. The pore sizes in the ultraporous thin film membrane diffusion barriers are in the range of from about 0.0005, but more often 0.001, to about 0.1 microns. In functional terms, the pores are small enough to prevent the enzyme from passing through but as large as possible, given that limitation, in order to allow for the maximum flow rate through the thin film membrane diffusion barrier. The properties of the thin film are determined by the specific properties of the selected polymer system employed, but with careful selection and good processing technique, it is possible to attain ultraporous thin film membrane diffusion barriers with physical and chemical properties appropriate to use in a wide variety of enzyme catalyzed and/or mediated diffusion reactions.

The ultraporous thin film membrane diffusion barriers are preferably made, in the present invention, by the formation of a thin polymer film under conditions where the polymer system is crosslinked to result in a controlled cross link density. The enzyme hydrogel and ultraporous thin film membrane diffusion barriers will most often be elements of composite structures, supported on a physical support which provides physical support and reinforcement for the gel and the thin film membrane diffusion barriers.

Figure 1:
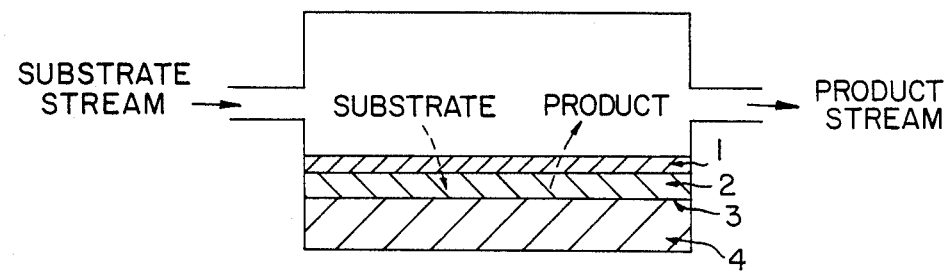
FIG. 1 shows a schematic reaction flow diagram, showing the operation of the present invention in its simplest embodiment and the simplest composite structure of the ultraporous thin film membrane enzyme reactor of the present invention.

The present invention will be described in detail below, referring to the accompanying drawings.

DETAILED DESCRIPTION OF THE INVENTION

In the present invention, the following terms are assigned the following specific meanings, unless a contrary meaning is made clear in the context of usage:

Molecular Weight Cutoff: An expression of the pore size and retention characteristics of a membrane in terms of molecules of known sizes. Pore size is rated as that molecular weight cutoff at which at least 90 percent of spherical, uncharged molecules of that same molecular weight will be retained by the porous membrane. However, linear molecules with molecular weights greater than the molecular weight cutoff may pass through the membrane, whereas charged molecules less than the molecular weight cutoff may not pass through. In the ultraporous thin film membranes employed in the present invention, particularly the ultraporous thin film diffusion barriers, the molecular weight cutoff ranges from 100 to 1,000,000.

Pore Size: In the case of ultraporous thin film membranes generally, there is considerable difficulty in directly observing and measuring pores and pore sizes, as by scanning electron microscopy, for example. It has become common in the art to employ molecular weight cutoff values as an inferential and indirect technique for the determination of pore sizes. As a general proposition, the diameter of pores is determined by the size of generally spherical, globular molecules passed through or retained by the membrane. The size of such molecules in Angstroms is approximately equal to the cube root of the molecular weight of the molecule. All pore sizes in the context of the present invention relating to the thin film membranes are determined by molecular weight cutoff values.

Pore Size of Ultraporous Membranes: Ultraporous membranes are generally those membranes having limiting pore sizes in the range of from about 0.0005, often 0.001 to about 0.1 microns in effective diameter, and fit into the spectrum of porous membrane media between the type generally considered to be reverse osmosis membranes and microporous membranes.

Enzymes are proteins which catalyze chemical reactions, either in vivo or in vitro. They function to lower the activation energy of chemical reactions. Without enzyme catalysis, many reactions necessary for the function and existence of living cells would either not take place or would destroy the cell if they did take place. Like other catalysts, enzymes generally function in low concentrations and can activate or promote both forward and reverse reaction rates without being consumed in the reaction. Unlike inorganic catalysts, enzymes are highly specific and generally act only on one specific substrate or class of substrates.

The specificity of enzymes is due in major part to the overall three dimensional structure of the protein molecule, which is in turn determined by the specific amino acids making up the molecule and their sequence. As part of the three dimensional structure of the enzyme there is a region, known as the active site, which is responsible for the catalytic activity. The nature of the three dimensional structure of the active site defines its physical and steric constraints, while the particular amino acids present at or near the active site determine the chemical nature of the site. Adjacent the active site, the three dimensional structure also defines regions known as binding sites. The binding sites allow for hydrogen bonding and polar or other electrical attractions between the enzyme and molecules with complementary chemical and physical structures. Because of the constraints defined by the active and binding sites, only specific molecules can meet the requirements of complementary structure, and only those complements can be activated by that specific enzyme. It is the molecules which are such complements which qualify as the substrate for a particular enzyme catalyzed reaction.

The very factors which allow for this high degree of substrate specificity are the same factors which are affected by changes in temperature, pH, the concentrations of substrate or product in the immediate environment of the enzyme, the presence of non-substrates which bind and block the site, and in the industrial context in particular, by cross linking or other reactions sometimes employed to immobilize the enzyme. Any technique for dealing with enzymes which alters the active site or the binding sites will change and/or destroy the capacity of the altered site to function in its original catalytic role.

When an enzyme and substrate interact, the substrate physically fits into the active site region and is held in place through the polar, hydrophobic, and hydrogen bonds which form between the substrate and the binding sites. The combination has a high affinity constant. The active site interacts with the immediately adjacent structure of the substrate to cause a change in the substrate, usually the breaking or formation of one or more chemical bonds, resulting in the formation of a product having a different, lower affinity constant. The product is not as close a complement, either chemically or physically, with the enzyme. Consequently, the product molecule is no longer bound, and the enzyme is left free and accessible to another substrate molecule for interaction and reaction.

Many enzyme-substrate combinations do reach an equilibrium point however, so that the accumulation of the reaction product in the system will eventually inhibit further production, either by virtue of the reversible nature of the reaction, or in some cases, by virtue of the blocking of the active site by binding to inactive near-complement sites on the product or the substrate molecules. Thus the reaction is concentration dependent both in relation to the substrate and particularly to the product.

In the adaptations of the reactions to bulk systems in industrial applications, there are a number of limitations of import. It is difficult to control the relative proportions of the enzyme and the substrate and product. It is generally desirable to provide for removal of the product from the system to avoid blockage of the active site by excessive accumulations which compete for access with the substrate and can thus inhibit the reaction. Separation of the product from the reactor stream, and particularly from the substrate, can be demanding. It is usually difficult and uneconomic to attempt to recover the enzyme from the system, and the activity is gradually lost as the reactive sites are blocked by the accumulations of by-products, impurities in the feed, accumulations of the reaction product, and physical and chemical wear and tear on the enzyme in the system from other factors. At a certain point, the reaction is terminated and the enzyme is discarded.

For many enzyme catalyzed reactions, the limitations of bulk reaction systems are not a problem, since many inexpensive enzymes are available that do not warrant concern over such limitations. In other contexts, however, there has been considerable interest and effort devoted to the development of effective immobilized enzymes. The objectives of such efforts are often the extension of the functional life of the enzyme, ease of separation and reuse of the enzyme, greater stability over a wider range of operating conditions, the avoidance of contamination of products, the capacity for continuous production, and improved purification of reaction products.

The immobilization techniques most frequently employed to achieve these objectives generally alter the activity, stability, specificity, reaction rates, or other properties of the enzyme, most often in an undesirable way. The procedures which avoid one set of difficulties have generally resulted in a different set of problems. Such procedures often reduce reaction productivity and add processing complexity and expense, as well as other difficulties, as is well known.

In the present invention, then, there is provided an enzyme reaction system which overcomes the major problems of bulk reaction systems without the introduction of the significant disadvantages of the prior art approaches to the problems.

In the present system, the enzyme is not required to be chemically or physically altered in any way, and retains its full desirable range of properties, particularly activity, specificity, and optimum operating conditions. The substrate and product are readily separated from the enzyme, so that there are no problems of product contamination with the enzyme. Neither product nor feed stream impurities accumulate beyond trivial levels, so that the active life of the enzyme is extended and surprisingly protracted, with no initial or gradual compromise in any of the properties. The reaction rates are high and do not materially decline over time. By use of some of the optional features of the present system, many reactions can be performed in a fashion that permits the continuous and substantially complete recovery of the reaction product in high purity and concentration in an effluent stream independent of the substrate feed, permitting highly economical and efficient product recovery virtually totally free of contamination by the enzyme, the substrate, and by impurities in the substrate feed. The reaction product can be recovered in most cases in sterile form, if desired, without sterilization of the substrate feed. The reactions can be performed in continuous process, with high feed throughput and high productivity, and by virtue of the specific nature of the reaction system can be implemented with simple and inexpensive equipment on virtually any scale of production required. In addition, the system is readily amenable to automation, and offers low labor and skill requirements in set up, initiation, operation, and maintenance. The system is adaptable to any enzyme and substantially any substrate, and is of general applicability. Operating conditions at the optimum for any specific enzyme-substrate combination can be readily accommodated.

These and still other advantages and objectives are provided in the present invention by virtue of the employment of the enzyme in the form of a hydrogel confined on a surface by a porous, ordinarily ultraporous, thin film membrane diffusion barrier. The aqueous substrate feed is passed over the thin film membrane surface, the substrate enters the reaction zone defined by the enzyme gel by diffusion through the thin film membrane diffusion barrier, and the reaction product diffuses out of the reaction zone and is recovered. Because of the particular properties of the thin film membrane diffusion barrier, the diffusion is very rapid and production rates are high.

Ultraporous membranes are widely used for a variety of procedures, including concentration driven, low pressure processes, including diffusion and ultrafiltration. In the context of enzymatic reactions they have frequently been employed in sterilization and purification of substrate feed streams, purification and concentration of product streams, and as physical containments for enzymes. Such usage differs materially from the present invention, however, since it is only by virtue of the recent development of ultraporous thin film membranes by one of the present inventors that the present invention became possible.

Reduced resistance to flow by diffusion through the membrane is probably the single most important feature of thin film membranes in the context of the present invention in comparison to the state of the art ultraporous membranes. The ability to closely control the pore sizes is of considerable import as well.

It has come as a considerable surprise and benefit that the ultraporous thin film membranes are exceptionally effective for molecular separations. While such procedures are sometimes performed with conventional ultraporous membranes, there is a rapid fouling and blockage of the membranes, ordinarily associated with plugging of the pores of the membrane structure which does not occur with the thin film ultraporous membranes. In the context of the present invention, advantage is taken of the effectiveness of the ultraporous thin film membranes to perform just such molecular separations.

An illustrative and schematic representation of the simplest embodiment of the ultraporous thin film membrane enzyme reactor of the present invention is shown in FIG. 1, wherein the thin film diffusion barrier 1 is shown supported on and confining enzyme gel layer 2, which in turn is supported on support 4, having surface 3.

In operation, the substrate, in an aqueous solution, is passed across the thin film surface in a continuous flow stream, as shown in FIG. 1. Since the concentration of substrate in the gel is initially zero, the concentration gradient causes diffusion of the substrate molecules through the thin film and into the enzyme hydrogel, as shown generally in FIG. 1. Conditions are maintained at suitable values for the enzyme-substrate reaction to proceed, preferably at or near optimum conditions for the reaction. As those of ordinary skill in the art will readily appreciate, the enzyme hydrogel constitutes a reaction zone under these conditions, where the enzyme will act on the substrate to produce the product. As the reaction proceeds, the concentration of the product in the enzyme hydrogel increases, and a concentration gradient for the product is established which drives the passage of the product out of the gel, through the thin film, and into the feed stream, as shown generally in FIG. 1. As those of ordinary skill in the art will readily appreciate, the concentration of substrate in the feed stream must be kept at a level high enough to sustain a concentration gradient which will continue to drive the diffusion of substrate into the enzyme gel, and, if the process stream is recirculated in continuous fashion, the product must be removed, as seen in FIG. 1, to sustain an appropriate concentration gradient to drive diffusion of the product out of the enzyme gel. It will be readily apparent as well that the thin film membrane diffusion barrier must have a pore size large enough to relatively freely pass the substrate and product through under the force of the diffusion process, but small enough to prevent the enzyme from passing through the thin film membrane diffusion barrier.

In this simplest form of the invention, the support is not involved other than in the role of providing an adequate physical structure to hold the enzyme gel and the thin film. In that context the support can be virtually any material which is substantially inert to the enzyme reaction system. It is desirable that it afford a high surface area for the thin film diffusion barrier and the underlying enzyme hydrogel, and it may be particulate, fibrous, or in the form of a flat surface. The support may be made of metal, glass, coated paper, polymer materials, or the like.

As those of ordinary skill in the art will appreciate, the simplest embodiment of the invention functions most efficiently if the support is dense or nonporous. If the support is nonporous, the product can only diffuse back into the feed stream which is preferred over allowing the product to diffuse into the support itself, something that is only possible if the support is porous. It is possible, however, to utilize a porous support and still have the reactor function efficiently if the surface of the support is first coated with an impervious coating or dense thin film which essentially makes the support nonporous. Such a coated porous support can be seen in the embodiment shown in FIG. 2, which is a variation of FIG. 1, wherein the support 4 is porous, preferably microporous, and has interposed between its surface 3 and the enzyme hydrogel 2 a second thin film membrane diffusion barrier 5, which shall also be referred to as the support surface thin film membrane. As in the simplest embodiment of the invention, the thin film diffusion barrier 1 is supported on and confines enzyme hydrogel layer 2. In this embodiment, the support surface thin film membrane is a dense thin film which serves to make the porous support impervious to the enzyme, substrate, and product. Possible porous supports which would be useful in this embodiment are the same as those discussed below in connection with the alternative embodiment shown in FIG. 3. The other components of this embodiment are discussed herein in connection with the embodiment shown in FIG. 1.

The enzyme is applied to the surface of the support as a hydrogel by deposition of a coating of appropriate thickness to the support surface. The aqueous enzyme coating forms a stable gel structure on the support surface.

The enzyme solution is deposited on the support, conveniently by dipping the support into a bath of the solution followed by spreading or draining or the like to remove excess, regulate thickness of the gel layer, and to assure a uniform, continuous coating on the support. The gel is formed by gellation.

The gel layer should be no thicker than is necessary to achieve a stable, continuous and active layer. Excessive thickness is generally wasted, since it will be the components of the system nearest the thin film membrane diffusion barrier layer which will be the most active. It is preferable to add additional surface area to increase productivity. In light of these criteria, the enzyme hydrogel layer will ordinarily be in the range of from about 1 to about 10 microns in thickness. If thinner hydrogel layers are employed, it is difficult to maintain the continuity of the layer, and in thicker layers, the rate of diffusion to the distant regions is too slow to contribute materially to the productivity of the system.

As an optional variation, the enzyme hydrogel may be formed by dissolving the enzyme in an aqueous solution of a hydrogel forming material, ordinarily a hydrogel forming polymer, followed by the application of a coating of the solution on the support, and then causing the solution to gel. Many such hydrogel materials are known to the art, and the present invention may be practiced with substantially any of the many natural and synthetic hydrogel forming polymers which meet a few simple and straightforward criteria.

The gel forming polymer must be chemically compatible with the enzyme reaction system, not susceptible to contamination of the product stream, capable of forming a stable gel which will include the enzyme and have a high porosity for water, substrate, and product. Preferably, the gel should have a much higher porosity than the thin film diffusion barrier. When the system is used in connection with food or pharmaceutical applications, it is generally necessary that none of the constituents be toxic. Many hydrogel forming materials are generally recognized as safe in such applications. In addition, it is preferred that the gel be at least partially cross linked if possible, and still more preferably that it be irreversibly bound to the support and to the thin film membrane diffusion barrier.

The preferred hydrogel forming polymers for use in this optional embodiment of the present invention include gel forming hydrophylic polymers and copolymers of monomers containing carboxylic acid groups, hydroxyl groups, amine groups, alginic acid, guar gum, and the like.

The enzyme and polymer solution is deposited on the support, conveniently by dipping the support into a bath of the solution followed by spreading or draining or the like to remove excess, regulate thickness of the gel layer, and to assure a uniform, continuous coating on the support. The gel is formed by gellation in known manner. Light cross linking, where possible is conducted either before or, preferably, after gellation. The enzyme is physically entrapped and confined within the gel, but does not materially react with the polymer or any of the gel forming constituents.

The concentration of the enzyme within the polymer gel is not a narrowly critical consideration, but as a general rule, if this variation is used, it is preferred that the concentration be as high as possible without interfering with or disrupting the physical or chemical integrity of the gel structure and its capacity to enhance the physical stability of the enzyme hydrogel layer. Most polymer gels will accommodate substantial proportions of the enzyme, up to as much as ninety percent of the total solids of the gel. The enzyme will ordinarily be included in an amount of from the slightest amount, sufficient to show enzymatic activity on the substrate, e.g. one percent, up to ninety percent of the solids content (dry weight) of the gel. Most often, the enzyme will be from about forty to about eighty, and preferably from about fifty to about seventy, weight percent of the dry gel.

It will be readily apparent to those of ordinary skill that the reactive capacity of an enzyme is determined by its activity, and not in terms of weight percent. Since activity varies widely among enzymes, the reactive capacity will be dependent on the nature of the enzymes employed.

As in the simplest embodiment, the enzyme and polymer hydrogel layer will ordinarily be in the range of from about 1 to about 10 microns in thickness.

The thin film membrane diffusion barrier layer is applied directly on the surface of the hydrogel layer, and is preferably formed in situ by one or more of the techniques discussed in detail in the application of Wolfgang J. Wrasidlo, ULTRAFILTRATION THIN FILM MEMBRANES, Ser. No. 920,365, filed Oct. 20, 1986, and incorporated by reference herein, particularly for the disclosure to those of ordinary skill in the art of the full range of variables and parameters which determine the making of the thin film and the properties thereof, but also with regard to the support structure, and other parameters of import herein. Preferred among these is the application to the surface of a relatively dilute solution of polyethylene imine, by dipping or the like, followed by draining the coating until a golden color forms, in about two to five minutes, followed by contacting the surface of the solution with an immiscible solution of toluene diisocyanate, preferably in hexane. The TDI reacts to cross link the PEI only at the interfacial boundary of the immiscible phases, and thus forms a thin film. By controlling the extent of the cross linking reaction, the pore size of the thin film is determined.

The pore size of the thin film should be greater than the effective diameter of both the substrate molecule and the product molecule, so that both these components can diffuse relatively freely through the diffusion barrier. At the same time, the pore size should be less than the effective diameter of the enzyme, so that it may not pass the barrier and remains entrapped in the hydrogel layer. It is important to recall that effective diameters for purposes of the present invention are different for highly linear molecules than for generally spherical or globular molecules, and the pore sizes of the membrane are applicable to generally globular molecules such as those employed for the determination of molecular weight cut off values by which the pore sizes are inferred. It is a relatively simple matter to determine the effective molecular diameter for any enzyme, substrate or product by measuring retention on filtration membranes of varying pore sizes, preferably by diffusion but if necessary by filtration under pressure.

Functionally, the maximum useful pore size is the largest which will retain the enzyme without detectable losses. Anything larger is ineffective. Any pore size much smaller than the maximum, increases flow resistance for the substrate and product diffusion is impeded. Thus, there is a disadvantage to a pore size any smaller than required.

As those of ordinary skill in the art will have recognized, it is the properties of the enzyme reaction system which will determine the specific parameters for use in the formation of the thin film membrane enzyme reactors of the present invention. With the guidance offered herein, it will be a simple matter to adapt the present invention to any enzyme system. It should be noted, however, that the present system is not applicable to any enzyme substrate reaction where the effective molecular size of the substrate and/or the reaction product are greater than the enzyme, since any thin film membrane diffusion barrier having a pore size effective to contain the enzyme in the hydrogel reaction zone will not in that case permit the effectively larger molecule to diffuse into and/or out of the reaction zone.

Diffusion through the thin film membrane diffusion barriers in the present invention is ordinarily rapid, so that the reaction can proceed at effective rates. The speed of diffusion is a direct consequence of the very thin structure of the diffusion barrier, so that the thinnest possible thin film membrane layers are preferred in the present invention. The capacity of the thin film membrane diffusion barriers to pass the substrate and product molecules without substantial plugging or clogging over time of the membrane pores is critical to sustaining the high levels of diffusion on which success is dependent.

It is preferred that the components of the thin film based enzyme reactor system of the present invention be made of polymer materials. In particular, the thin film membrane diffusion barriers are formed of cross linked polymer materials. The pore size of the thin film membrane diffusion barriers is controlled by controlling cross link density, as set forth in more detail in Wrasidlo, ULTRAFILTRATION THIN FILM MEMBRANES, Ser. No. 920,365.

The polymer systems for use in the thin film membrane diffusion barrier of the present invention are all those cross linked polymer species employed in the formation of membranes. As those of ordinary skill in the art will recognize, the selection of polymer and cross linking systems will most often depend on the intended environment of use and the service duty required of the ultraporous thin film membrane diffusion barriers. A wide diversity of such materials and systems is known. See for example, Kesting, Robert E., *Synthetic Polymeric Membranes: A Structural Perspective*, 2d. Ed., Wiley-Interscience, New York, 1985. Only cross linked systems are a part of the present invention, but as that term is employed herein, it is intended to include those polymers formed from monomers which cause, at least in part, a high degree of branching to provide integral cross linking as a part of the polymer structure, particularly those formed in interfacial condensation polymerizations, as well as reactions of polymers with cross linking reagents which tie different polymer molecular chains together. Such polymers include, generally any crosslinkable member selected from the group consisting of polysaccharides, polysilicones, polycarbonates, polyamides, polyacrylics, polyimines, polyethers and polysulfones.

It will most often be preferred or necessary to employ polymers which are available in forms which are soluble in solvents, to facilitate the formation of thin films of the polymer solution and thereafter to cross link the polymers with a cross linking reactant at the interface with a separate phase in an interfacial reaction. Typical of this class of polymer systems is the preferred system in the present invention, an aqueous solution of polyethylene imine, which is then spread in a thin layer on the surface of a supporting medium, and thereafter contacted with a dilute solution of toluene diisocyanate in hexane to form polyurea cross links. This preferred polymer system is the basis of much of the discussion herein, and is sometimes referred to as the PEI/TDI polymer system.

Also of considerable interest is the polyamide resulting from cross linking of the PEI with isophthaloyl dichloride, sometimes referred to as the PEI/IPC polymer system.

Other polymer systems of interest are the fully aromatic polyamides formed by interfacial condensation polymerization from epiamine, m-phenylene diamine and other diamines and the like, condensed with IPC and/or TMC, and a variety of other related species. This system is typical of the formation of ultraporous thin film membranes from monomeric systems.

When the thin film membrane diffusion barrier is a polyelectrolyte, it will effect a pH optimum shift for the enzyme. Depending on the charge density, the shift can be as much as one pH unit. The direction of the shift is dependent on the polarity of the charge. This characteristic of the thin film membrane diffusion barrier provides an additional means to control the pH shift and pH optimum of the enzyme by choosing the appropriate charge polarity and charge density of the thin film polymer.

In use, the enzyme reactor structure defined by the composite of the ultraporous thin film membrane diffusion barrier, the intermediate enzyme hydrogel layer, and the support, will be incorporated into a physical containment reactor vessel for use. The vessel should be designed to accommodate a very large surface area, since it is the surface area which will be the primary determinant of the reactor production capacity. A variety of constructions are known to those of ordinary skill in the art, and it is possible to adapt any of them in self evident fashion to the requirements of the enzyme reactor of the present invention. It is preferred, when the support is not porous, to form the enzyme reactor either on a fibrous, i.e. glass fiber, support, or in other circumstances, on thin flat plates of films of supporting materials. In the case of fibrous supports, the reactor vessel is quite simple, requiring only a vessel with an inlet and and outlet. As shown in FIG. 1, the fibrous enzyme reactor is packed inside the vessel, and the feed steam is pumped through the reaction vessel at an appropriate rate. The effluent stream is processed to recover the product, and the unreacted feed stock is preferably recycled.

In the case of thin plate forms, it is readily apparent the enzyme hydrogel and thin film membrane diffusion barrier are desirably applied to both faces of the plates, which are then mounted in a reactor vessel in a spaced array suitable to define flow paths for the feed-effluent stream to pass therebetween.

In either case, the control of the conditions of the reaction, by controlling the composition of the feed stream, the pH, temperature, and like enzymatic reaction determinants, are all well within the ordinary skill of the art. Likewise, the recovery of the product from the reaction vessel effluent stream is well known technology to those of ordinary skill. Neither of these aspects of the reaction forms any part of the present invention.

Figure 3:
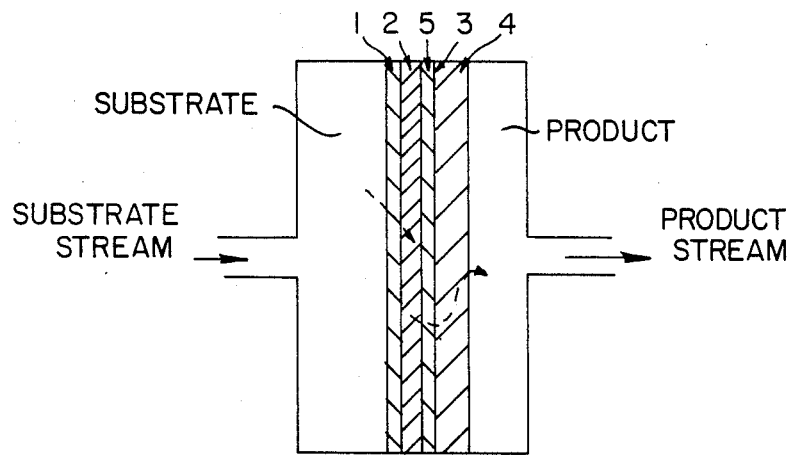
FIG. 3 shows a schematic reaction flow diagram, showing the operation of the invention in its flow through embodiment and another embodiment of the structure of the ultraporous thin film membrane enzyme reactor of the present invention.

In an alternative embodiment of the present invention, shown in FIG. 3, the support 4 is porous, preferably microporous, and has interposed between its surface 3 and the enzyme hydrogel 2 a second thin film membrane diffusion barrier 5, which shall also be referred to as the support surface thin film membrane. As in the simplest embodiment of the invention, the thin film diffusion barrier 1 is supported on and confines enzyme hydrogel layer 2. In this alternative embodiment, particularly in enzyme reactions which result in a product molecule smaller than the substrate molecule, the pore sizes of the two thin film membrane components will be different, so that the substrate can diffuse through the thin film membrane diffusion barrier on the feed stream side, as shown in FIG. 3, but not through the support surface thin film membrane, while the smaller molecules of the reaction product can diffuse through both, but particularly through the support surface thin film membrane into a product stream where the product is recovered free of substrate, as shown in FIG. 3. In this case, the increment of product which initially diffuses into the feed stream is allowed to accumulate, so that the concentration reaches, over time, an equilibrium level in relation to the gel concentration, and diffusion into the feed stream then ceases, and the only concentration gradient will be with the product stream.

The support in this embodiment is necessarily porous, particularly microporous. Within limits, the support may be made of a wide diversity of materials. Preferred supports are those integral, skinned synthetic polymer microporous membranes, composed of a diversity of polymer materials, including polysulfones, polyether sulfones, polyvinyl chlorides, chlorinated polyvinyl chlorides, diverse polyamides, polyesters, polycarbonates, polyurethanes and polyureas, polysilicones, cellulose derivatives, and the like.

Particularly preferred are the polysulfone membranes available from Brunswick Technetics as BTS polysulfone, and those disclosed in European Patent Office Application 81/301074, and in U.S. application Ser. No. 130,560, filed Mar. 4, 1980 and Ser. No. 291,927, filed Aug. 11, 1981, the disclosures of which are incorporated herein by reference.

The microporous membranes used as the preferred supports in the present invention are characterizable as reticular, highly asymetric, having exceptionally good permeability and unusually low resistance to flow for a given pore size. In addition, these preferred supports have unusually smooth and regular skin surfaces, and high pore densities and are thus near ideal support structures for the ultraporous thin film membrane diffusion barriers of the present invention.

As in the case of the selection of polymer systems for the ultraporous thin film membrane diffusion barriers, it will also be appropriate to select the support membrane polymer for its suitability for the intended environment of use. Those of ordinary skill in the art will be able to make the selection from among the suitable materials as is customary in the membrane art. The polysulfones and polyether sulfones are generally preferred for most applications, for the reasons already well known to those of ordinary skill in the art, including their ready availability, their desirable physical and chemical properties, and particularly in food service and pharmaceutical usages, their status of being generally recognized as safe for such applications.

It is also appropriate to select support structures with a view to the physical demands of the intended use and the needs and requirements of the ultraporous thin film membrane diffusion barriers to be supported. It is important, for example, that the support afford a smooth supporting surface, free of large expanses which require the ultraporous thin film membrane diffusion barriers to bridge large pores or other artifacts on the support surface. This requirement will ordinarily dictate that the support be skinned, and preferably that it have a very smooth skin. The pores of the support skin should be, preferably, on the order of about 0.1 to 0.5, more preferably from about 0.1 to 0.2 microns in diameter. Larger pores impose great physical burdens on the ultraporous thin film membrane diffusion barriers by the requirement that the large spans across the pores must be self supporting, and therefore the span should be no larger than necessary. Smaller pores, below about 0.1 micron, are generally undesirable since they then would tend to contribute to limiting porosity of the composite, and retard flow rates through the composite to a degree to be avoided if possible.

It is also possible to improve on the characteristics of the ultraporous thin film membrane supports in this alternative embodiment of the present invention, and particularly their physical integrity, by interposing between the support surface ultraporous thin film membrane and the support a thin, freely porous gel layer, the intermediate support gel layer. The intermediate support gel layer, when employed, will provide an intermediate aid to bridging the pores of the support, improve flow properties in some cases, and in appropriate circumstances, permit the formation of composites of otherwise incompatible supports and membrane polymer systems. All these features, and others, are discussed in detail hereinafter.

Given the dimensions of the thin films in the present invention, while they are a material advance in physical integrity and strength in comparison with the prior art thin films, they are, nonetheless, relatively fragile structures in an absolute sense. For many polymer systems, the integrity of the thin film can be greatly enhanced by the provision of a gel layer to aid in bridging the pores of the support. Particularly for monomolecular thin films, it is noteworthy that a film which is 0.0015 microns thick may be required to bridge a pore diameter of 0.1 microns or more. It is readily apparent that when the thickness of the film is on the order of only 1.5% of the span, the physical demands are considerable.

In that context, it is apparent that the provision of an intermediate support gel layer, which forms an intermediate supporting structure, can be of considerable assistance in improving the physical support for the support surface thin film membrane layer.

In another context, some microporous support layers have limited pore densities on the surface, and when the support surface thin film membrane is in direct adherent contact with the surface, only those areas of the support surface thin film membrane which directly overlie the pore area are able to function; the other areas of the support surface thin film membrane will be blocked by the dense surface of the support. In that eventuality, an intermediate support gel layer will provide a flow path from such "blocked" areas of the support surface thin film membrane to an adjacent pore of the support.

When such intermediate support gel layers are employed, it is desirable that the thickness of the layer, in hydrated form be sufficient to afford the physical parameters required, and no more. While this will be very much greater than the dimensions of the support surface thin film membrane, it will ordinarily be on the order of about 0.1 to 5, and preferably about 0.5 to 2, microns in the gel state, less in the event the gel is dried. Thinner intermediate support gel layers introduce the risk of the gel layer being discontinuous, while thicker layers unacceptably increase the resistance to flow.

The specific demands of the environment of use will ordinarily dictate the particular requirements of the intermediate support gel layer. When used in an aqueous environment the intermediate support gel will necessarily be a hydrogel. The polymer employed must be gel forming in the media with which it will be used. The gel must have a porosity greater than that of the ultraporous support surface thin film membranes with which it is employed. It must resist degradation and attack in the context of use. It must have adequate resistance to pressure to avoid excessive compression or compaction in use at the pressure differentials needed for the service. It must not have components soluble in the context of use which could contaminate the media being processed, and must not interact in any impermissible way with the process stream in use.

With these criteria in mind, those of ordinary skill in the art will recognize that a wide diversity of polymer materials can be employed, including of course all those mentioned above for the selection of the thin film forming polymers. In addition, a wide diversity of cross linkable gel formers are known. Exemplary of those are the gel layers in the applicant's disclosure in U.S. patent application, Ser. No. 892,050, filed Aug. 1, 1986, a Continuation of Ser. No. 526,811, filed Aug. 26, 1983, a Continuation in Part of S.N. 225,348, filed Jan. 15, 1981, the disclosure of which gels, and the formation and behavior of which, is hereby incorporated by reference herein.

Taken in combination, the usual structures in the present invention are made up of a composite of the foregoing components, i.e. the ultraporous thin film membrane diffusion barrier, the intermediate enzyme hydrogel layer, and the support. In preferred circumstances, the support is one of the composite thin film membranes disclosed and claimed in Wrasidlo, ULTRAFILTRATION THIN FILM MEMBRANES, Ser. No. 920,365. The intermediate enzyme hydrogel layer is the same as the enzyme hydrogel layer or the enzyme and polymer hydrogel layer discussed previously in connection with FIG. 1.

As already noted, the preferred technique for the formation of the ultraporous thin film membrane diffusion barriers of the present invention resides in the now well known technique of interfacial polymerization. This is also true for the formation of the ultraporous support surface thin film membranes found in this embodiment of the invention. Interfacial condensation polymerization has been employed to obtain thin films with a variety of polymer systems. See for example, Morgan, *Condensation Polymers: By Interfacial and Solution Methods*, Interscience, New York, 1965. Those of ordinary skill in the art will gain substantial guidance in the techniques for the practice of the present invention there. See also Kesting, Robert E., *Synthetic Polymeric Membranes: A Structural Perspective*. 2d. Ed., Wiley-Interscience, New York, 1985, for further discussions concerning the relevant considerations in the context of porous thin films.

It is central to the present invention, however, that the techniques of interfacial condensation are not, as is usual in the membrane art, permitted to proceed to a fully cross linked state in order to provide a thin film membrane. By one or more of the techniques discussed herein, the procedure is modified to produce ultraporous thin film membranes by virtue of control of the cross link density in the resulting thin film, through regulating the determinants of cross link formation.

Cross link density is, in the context of the present invention, the level of cross linking appropriate to produce pores in the ultraporous thin film membranes of the desired size, having a molecular weight cutoff of about 500. The desired pore size will vary depending on the enzyme used in the reactor. The size of the pores should be small enough to prevent the enzyme from passing through the pores yet large enough to allow for the best possible flow rate of substrate and product through the ultraporous thin film membrane. For any given polymer system, the appropriate cross link density can be quantified, based on known parameters, known to those of ordinary skill in the art. For the cross linking of polymers, the major parameters which are the determinants of cross link density will often be, for example, polymer or oligomer concentration, the thickness of the film of the polymer solution on the support, the molecular weight or degree of polymerization, the nature, reactivity, and frequency within the polymer chain of cross linking reactive sites, the particular nature and concentration of the cross linking agent, and the like. In interfacial condensation polymerization, the degree of branching, and thus of the formation of cross linking branches is often determined by the functionality and proportions of cross linking monomers, and of chain transfer and chain termination agents. As a general proposition, then, the greater the degree of cross linking produced in the polymer system, the smaller the pore sizes. It is a relatively simple exercise for those of ordinary skill in the art to ascertain the appropriate degree of cross linking for a desired pore size, given the guidance of the related application of Wrasidlo, ULTRAFILTRATION THIN FILM MEMBRANES, Ser. No. 920,365, and incorporated by reference herein, to regulate the determinants of the cross link density of the polymer system accordingly.

It is a part of the present invention to provide techniques for the control of cross link density in the thin films to assure that the required limiting pore sizes in the ultraporous range in relation to the desired substrate and reaction product are attained. There are four fundamental techniques that have been employed alone and in combination. These are, for convenience, designated as reactant concentration control, time and temperature control, solution property control, and cross link disruption. As those of ordinary skill in the art will recognize, the effectiveness of each of these techniques will be dependent on the properties and nature of the particular polymer system employed. The adaptation of a particular system to the requirements of these procedures will, given the guidance of the instant application, be well within the level of ordinary skill in the art.

With the selection of appropriate materials and pore sizes, the ultraporous thin film membrane diffusion barriers or the ultraporous support surface thin film membranes of the present invention are particularly desirable for use in molecular separations in the embodiment of the present invention using two thin film membranes, where particular advantage can be taken of the low flow resistance as well as the relative freedom from plugging and fouling to permit the separate recovery of the product through diffusion through the support surface thin film membrane and through the support into a product stream which remains free of the substrate. A molecular separation occurs at the support surface thin film membrane, driven by the concentration gradient of the product between the hydrogel and the product stream. In this circumstance, the structure is best achieved by the employment of one of the supported thin film membrane composites disclosed and claimed in Wrasidlo, ULTRAFILTRATION THIN FILM MEMBRANES, Ser. No. 920,365. The enzyme hydrogel is applied directly on the surface of the support surface thin film membrane, and the feed stream diffusion barrier is another thin film membrane formed, preferably in situ, on the surface of the enzyme hydrogel. In this context, the support may contain an integral intermediate support gel layer as a part of its structure or if appropriate, the intermediate support gel layer may be omitted.

For those enzyme-substrate reactions which result in cleavage of the substrate molecule, as in the case of lysis reactions in general, as well as others, it is often the case that the product molecule or molecules are smaller than the feed substrate molecule in their effective molecular diameter. When such conditions are present, it will often be possible and even preferred to use the alternate embodiment of the present invention wherein the support is a porous diffusion barrier itself. As already discussed, the preferred support for this embodiment is, in any such case, a composite ultraporous thin film membrane on a microporous support. The reactor vessel in that case will be more complex, as shown schematically in FIG. 3. It is necessary to establish plural streams, of substrate feed and effluent, and additionally a product stream feed and effluent. In operation, the substrate feed, rich in substrate, is pumped into the vessel, following a flow path across the feed diffusion barrier surface, and the stream, depleted in substrate then passes out of the vessel. As previously discussed, the substrate molecules diffuse from the high concentration feed stream through the thin film membrane diffusion barrier, into the relatively low concentration enzyme hydrogel reaction zone, where the reaction between substrate and enzyme occurs. While, initially, the product formed will diffuse into the low concentration substrate stream, the level builds until an equilibrium level of concentration is established, and lacking a concentration gradient, no net diffusion of the reaction product into the substrate feed occurs once that condition is established. In a second flow path, in diffusive contact with the porous support, there is established a flow of water or other aqueous solvent for the reaction product, maintained with a low concentration of the reaction product. Thus a substantial concentration gradient is established between the product in the enzyme hydrogel reaction zone and the product flow stream, and diffusion of the product through the support surface thin film membrane will occur. The high permeability of the microporous support layer aids in facilitating the product diffusion, although it is important that the microporous support be no thicker than essential, since the distance over which the diffusion must occur is a factor in the production rate of the system. The product is continuously recovered from the product effluent stream. With appropriate selection of pore sizes in the diffusion barrier layers, none of the substrate will diffuse into the product stream, and the product recovery and purification will be greatly facilitated. The capacity of the present system to perform and sustain such a molecular separation of substrate and product is a major advantage of the low incidence of plugging and fouling of the thin film ultraporous diffusion barriers employed in the present invention.

Figure 4:
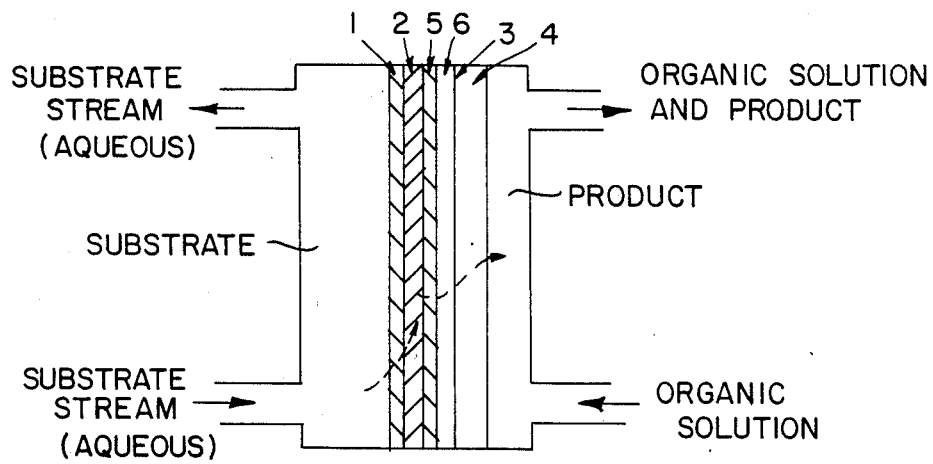
FIG. 4 shows a schematic reaction flow diagram, showing the operation of the invention in its extraction embodiment and yet another embodiment of the structure of the ultraporous thin film membrane enzyme reactor of the present invention.

Variations of this flow through embodiment of the enzyme reactor are possible. For example, non-aqueous solvents such as hexane or toluene may be used as the product feed and effluent. This variant, as shown schematically in FIG. 4, allows for the extraction of product in cases where the substrate is insoluble or nearly so in the non-aqueous solvent, or not able to pass through the support thin film, or otherwise not able to get into the product extract. The enzyme reactor shown in this embodiment is similar to that shown in FIG. 3. The support 4 is porous, preferably microporous, and has interposed between its surface 3 and the enzyme hydrogel 2 the support surface thin film membrane 5. As in the simplest embodiment of the invention, the thin film diffusion barrier 1 is supported on and confines enzyme hydrogel layer 2. In this embodiment, there is found between the support surface thin film membrane 5 and the support surface 3 a thin, freely porous gel layer, the intermediate support gel layer 6. The components of this embodiment are described in more detail above, in connection with the description of the embodiment shown in FIG. 3.

The opposite variation, using a non-aqueous substrate feed and effluent and an aqueous product feed and effluent, is also useful in certain situations. It is also theoretically possible to have both the substrate feed and effluent and the product feed and effluent be non-aqueous solvents. This would be effective where the substrate is highly soluble in the enzyme hydrogel inside the thin film membrane diffusion barrier, and the product is not. In this case, the product would be less likely to diffuse back into the enzyme hydrogel layer. If appropriate solvents were chosen, the substrate would not likely diffuse through the support into the non-aqueous product solvent. Although this variation, using various combinations of aqueous and non-aqueous solvents, is similar to an extraction, the actual transport of the substrate and product across the thin film membranes will be different from a liquid-liquid extraction. The partition coefficient of solubility which controls the extraction of substrate and product will be affected by the need to diffuse the substrate or product through the thin film diffusion barrier membrane and the support surface thin film membrane.

In practice, the reactor vessel will be packed with a large number of the plate and separator elements, maximizing for the construction employed the diffusion surface areas of the composite elements, and thus maximizing the reactor through-put capacity and productive capacity. The structural concept shown schematically in the figures can readily be adapted by those of ordinary skill to a wide variety of reaction vessels, including plate and frame reactors, tube and manifold reactors, spiral wound cartridge configurations, and the like.

The reactors of the present invention can function at low pressures. However, while diffusion proceeds on the basis of concentration gradient alone, and the process does not require pressure beyond that to cause flow of the streams through the reactor vessel, as those of ordinary skill in the art know, many enzyme reactions are conducted at elevated pressure. When the circumstances admit, it is desirable to operate the reaction system of the present invention at elevated pressures, up to 100 p.s.i. The higher the molecular weight cutoff of the ultraporous membranes, the lower the pressure needed to create a pressure differential across the membrane. It is preferred to establish a pressure gradient from the substrate feed through the enzyme hydrogel reaction zone to the product removal stream. A net flow of water through from the higher pressure to the lower pressure zone will result, and the removal of the product from the reaction zone will be facilitated by this flow. The efficiency and productivity of the system can be greatly enhanced by this effect, which is, as those of ordinary skill in the art will recognize, a removal of the product from the reaction zone by molecular sieving, a most surprising aspect of the sustained operation of the present system.

As those of ordinary skill in the art will appreciate, one of the greatest benefits of the present system is that the enzyme acts in its unaltered form, and will react in a highly predictable fashion to all the usual and customary parameters employed to control enzyme catalyzed reactions. Among these are the control of pH, temperature, pressure, ionic strength, electrical charges, and a variety of activating and inhibiting constituents, such as metal ion activators, cofactors and coenzymes, stabilizers, and competitive and irreversible inhibitors, substrate concentration, product accumulation and the like. These parameters of enzymatic reactions are well known. It is important to note that any factor which is needed in the reaction zone must either be available from the feed by diffusion, or must be incorporated into the hydrogel at the time of its formation if it cannot diffuse through the thin film membrane diffusion barrier.

EXAMPLES

Example I

Yeast invertase was selected as a representative enzyme for purposes of demonstrating the present invention. The enzyme catalyzes the hydrolytic cleavage of sucrose to glucose and fructose. High fructose syrups are of considerable interest and utility in the food industry for enhancing sweetness of foodstuffs, particularly fruit juices, soft drinks, candies and the like, without increasing caloric content.

The enzyme employed is a commercially available exocellular invertase, Sigma I-4504, having a molecular weight of 270,000, and an activity of 310 AU/mg. One AU, or Activity Unit, equals 1 micromole sucrose converted per minute. The enzyme has been well characterized and is widely used in commercial applications.

As a support, a microporous commercially available membrane, Brunswick Technetics BTS 55, was provided with a support surface dense thin film coating formed of 1% PEI cross linked with 1% TDI. Such a thin film has a cross link density such that the thin film is ordinarily dense, but at high pressure may be porous, e.g. under reverse osmosis conditions, and will not pass water through the membrane at the pressures below at least several hundred psi. The support was formed following the procedure of Wrasidlo, ULTRAPOROUS THIN FILM MEMBRANES, as set out in Examples 1–6, incorporated by reference herein.

The enzyme was dissolved in water, at a concentration of one weight percent. The support was then coated with the resulting enzyme solution. The coated support was drained for five minutes in a vertical position and then allowed to stand, at ambient conditions for two hours, during which time the enzyme solution gelled.

The enzyme hydrogel coated support was then dipped into a solution of 0.5% PEI in water, drained for about three minutes, until a uniform gold color appeared on the surface. The composite was then contacted with a 0.1% solution of TDI in hexane on the PEI coated surface for 30 seconds, the resulting composite was washed with water, and dried at ambient conditions.

Figure 2:
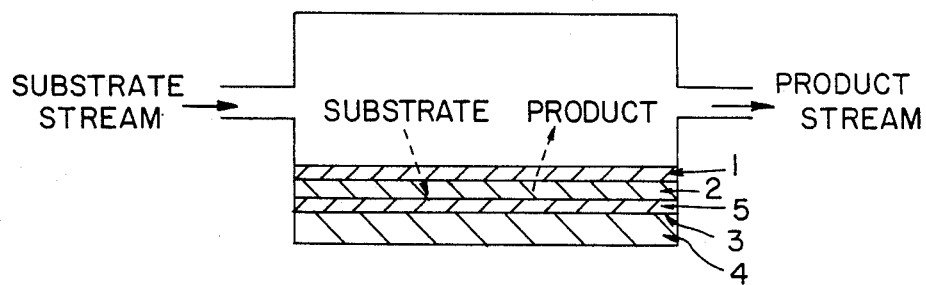
FIG. 2 shows the same schematic reaction flow diagram as FIG. 1, with a variation of the simplest composite structure of the ultraporous thin film membrane enzyme reactor of the present invention.

The composite enzyme hydrogel reactor thus formed was mounted in a cross flow reactor vessel, corresponding to FIG. 2, and an aqueous solution of sucrose was pumped across the face of the thin film diffusion barrier at pH 4.5, and at ambient temperature. The system showed a specific conversion of sucrose at 95 micromoles per minute, sustained for a period of twenty four hours with no detectable change in activity, and no detectable enzyme loss into the product stream.

What is claimed is:

1. An enzyme reactor consisting essentially of:
   a support;
   an enzyme hydrogel layer physically entrapped on said support; and
   a porous thin film diffusion membrane on said enzyme hydrogel layer, wherein said thin film diffusion membrane has a thickness of from about 0.0012 to 0.2 microns and a pore size sufficient to permit diffusion of a substrate for said enzyme and of the product of a reaction of said substrate catalyzed by said enzyme, but which will not permit said enzyme to pass through said thin film diffusion membrane, said thin film diffusion membrane adapted to direct exposure of a process stream.

2. The reactor of claim 1, wherein said support is impermeable.

3. The reactor of claim 1, wherein said support comprises:
   a support surface thin film layer in contact with said enzyme which is impermeable, and
   an open porous layer physically supporting said support surface thin film layer.

4. The reactor of claim 1, wherein said support comprises:
   a support surface thin film layer in contact with said enzyme which is porous to the product of a reaction of a substrate and said enzyme, but which will not permit said enzyme to pass through said support surface layer, and
   an open porous layer physically supporting said support surface thin film layer.

5. The reactor of claim 4, wherein there is interposed between said support surface thin film layer and said open porous layer physically supporting said support surface thin film layer a thin, freely porous gel layer.

6. The reactor of claim 1, wherein said support comprises: a support surface thin film layer in contact with said enzyme which is porous to the product of a reaction of a substrate and said enzyme, but which will not permit said substrate or said enzyme to pass through said support surface layer, and an open porous layer physically supporting said support surface thin film layer.

7. The reactor of claim 6, wherein there is interposed between said support surface thin film layer and said open porous layer physically supporting said support surface thin film layer a thin, freely porous gel layer.

8. The reactor of claim 1, wherein said support is a dense support having a high surface area per unit volume.

9. The reactor of claim 1, wherein said enzyme hydrogel comprises an aqueous gel of an enzyme and a hydrogel forming polymer.

10. The reactor of claim 9, wherein said hydrogel forming polymer is cross linked.

11. The reactor of claim 9, wherein said hydrogel forming polymer is irreversibly bound to said support and to said thin film membrane.

12. The reactor of claim 9, wherein said enzyme is physically entrapped in said hydrogel forming polymer in an amount of from about 10 to about 90 weight percent of said hydrogel forming polymer, on a solids basis.

13. A method for using an enzyme reactor the steps consisting essentially of:
   forming an enzyme reactor which comprises:
   a support;
   an enzyme hydrogel layer physically entrapped on said support; and a porous thin film diffusion membrane on said enzyme hydrogel layer, wherein said thin film diffusion membrane has a thickness of from about 0.0012 to 0.2 microns and a pore size sufficient to permit diffusion of a substrate for said enzyme and of the product of a reaction of said substrate catalyzed by said enzyme, but which will not permit said enzyme to pass through said thin film diffusion membrane;

placing said enzyme reactor into a reactor vessel;

dissolving substrate for said enzyme in a solvent therefor;

passing said dissolved substrate through said reactor vessel in such a manner that said substrate and said solvent therefor are in direct exposure to said porous thin film diffusion membrane;

allowing said substrate to interact with said enzyme, thereby forming a product;

collecting the product of said interaction of said substrate and said enzyme.

14. The method of claim 13, wherein said substrate diffuses through said thin film diffusion membrane and into said enzyme hydrogel layer prior to interacting with said enzyme.

15. The method of claim 13, wherein said product is collected by allowing said product to diffuse from said enzyme hydrogel layer through said thin film diffusion membrane and into said solvent for said substrate.

16. The method of claim 13, wherein said support further comprises
 a support surface thin film layer in contact with said enzyme which is porous to the product of a reaction of a substrate and said enzyme, but which will not permit said subsrate or said enzyme to pass through said support surface layer, and
 an open porous layer physically supporting said support surface thin film layer.

17. The method of claim 16, wherein said substrate diffuses through said thin film diffusion membrane and into said enzyme hydrogel layer prior to interacting with said enzyme.

18. The method of claim 16, wherein there is a solvent for said product in contact with the surface of said open porous layer of said support which is not in contact with said support surface thin film layer.

19. The method of claim 18, wherein said product diffuses through said support surface thin film layer and said open porous layer of said support into said solvent for said product.

20. The method of claim 18, wherein said said substrate is soluble in said solvent for said product.

21. The method of claim 18, wherein said substrate is insoluble in said solvent for said product.

22. The method of claim 18, wherein said product is insoluble in said solvent for said substrate.

23. The method of claim 16, wherein there is interposed between said support surface thin film layer and said open porous layer physically supporting said support surface thin film layer a thin, freely porous gel layer.

24. The method of claim 23, wherein there is a solvent for said product in contact with the surface of said open porous layer of said support which is not in contact with said support surface thin film layer.

25. The method of claim 23, wherein said product diffuses through said support surface thin film layer and said open porous layer of said support into said solvent for said product.

26. The method of claim 23, wherein said said substrate is soluble in said solvent for said product.

27. The method of claim 23, wherein said substrate is insoluble in said solvent for said product.

28. The method of claim 23, wherein said product is insoluble in said solvent for said substrate.

* * * * *